(12) United States Patent
Wilson

(10) Patent No.: US 8,865,926 B2
(45) Date of Patent: Oct. 21, 2014

(54) PROCESS FOR THE PRODUCTION OF CYCLOSILOXANES

(75) Inventor: Michael E. Wilson, Middleburg, FL (US)

(73) Assignee: SiVance, LLC, Spartanburg, SC (US)

( * ) Notice: Subject to any disclaimer, the term of this patent is extended or adjusted under 35 U.S.C. 154(b) by 263 days.

(21) Appl. No.: 13/244,990

(22) Filed: Sep. 26, 2011

(65) Prior Publication Data

US 2013/0079539 A1 Mar. 28, 2013

(51) Int. Cl.
*C07F 7/21* (2006.01)

(52) U.S. Cl.
CPC .................................... *C07F 7/21* (2013.01)
USPC ............ 556/460; 556/450; 556/461; 556/462

(58) Field of Classification Search
USPC .................................. 556/450, 460, 461, 462
See application file for complete search history.

(56) References Cited

U.S. PATENT DOCUMENTS

| | | | |
|---|---|---|---|
| 3,557,177 A | 1/1971 | Selin | |
| 3,590,064 A | 6/1971 | Lacefield | |
| 5,247,116 A | 9/1993 | Buese et al. | |
| 5,491,249 A | 2/1996 | Kostas | |
| 5,670,689 A | 9/1997 | Allandrieu et al. | |
| 6,593,500 B2 | 7/2003 | Priou et al. | |
| 7,148,370 B1 | 12/2006 | Rubinsztajn et al. | |
| 2003/0139287 A1* | 7/2003 | Deforth et al. ................. | 502/202 |
| 2004/0127668 A1 | 7/2004 | Rubinsztajn et al. | |
| 2005/0033001 A1* | 2/2005 | Cella et al. ...................... | 528/16 |

FOREIGN PATENT DOCUMENTS

DE 19619002 A1 11/1996

OTHER PUBLICATIONS

Chrusciel, J. et al., Dehydrocondensation of Organic Hydrosilanes With Silanols, Part I. Kinetics and Mechanism of the Reaction in Dimethlformamide. *Polish Journal of Chemistry*, vol. 57, 1983, pp. 113-120.
Chrusciel, J. et al., "Dehydrocondensation of Organic Hydrosilanes With Silanols, Part II. Effect of Siloxane Chain Length on the Reactivity of Si—H End-Groups. The Substitution Effect". *Polish Journal of Chemistry*, vol. 57, 1983, pp. 121-128.
International Search Report of PCT/US2012/056841 filed on Sep. 24, 2012, 4 pages.
Written Opinion of the International Searching authority for PCT/US2012/056841 filed on Sep. 24, 2012, 4 pages.
Chrusciel, J, et al.,"Dehydrocondensation of Organic Hydrosilanes With Silanols. Part II. Effect of Siloxane Chain Length on the Reactivity of Si—H End-Groups. The Substitution Effect," *Polish Journal of Chemistry*, 1983, pp. 121-127, vol. 57, No. 121.

\* cited by examiner

*Primary Examiner* — Sudhakar Katakam
*Assistant Examiner* — Pancham Bakshi
(74) *Attorney, Agent, or Firm* — Robert M. Lanning

(57) ABSTRACT

Embodiments of the invention are directed to the preparation of a discrete cyclosiloxane or a discrete mixture of cyclosiloxanes where a dihydroxysilane or dihydroxysiloxane condenses with a dihydrosilane or dihydroxysiloxane in the presence of a Lewis acid catalyst in a reaction phase including a solvent. The introduction of the dihydroxysilane or dihydroxysiloxane and dihydrosilane or dihydroxysiloxane is controlled such that the cyclocondensation occurs in a reaction phase that is dilute in the SiH and SiOH functionality permitting the isolation of the monocyclocondensation adduct in high yield with little higher molecular weight condensation products. In one embodiment of the invention 1,1-diphenyl-3,3,5,5-tetramethylcyclotrisiloxane is prepared in very high yield.

12 Claims, No Drawings

PROCESS FOR THE PRODUCTION OF CYCLOSILOXANES

BACKGROUND OF INVENTION

Cyclosiloxanes are prepared by a number of processes. Hydrolysis of dialkyldichlorosilanes, RR'SiCl$_2$, comprises the original process and is practiced on the industrial scale. Hydrolysis often yields complex mixtures of liner and cyclic siloxanes, with cyclotetrasiloxanes formed in the highest proportion and with little formation of cyclotrisiloxane. (see W. Noll, "Chemistry and Technology of Silicones", Acad. Press, 1968).

An alternate process for the preparation of cyclosiloxanes is acid or base-catalyzed depolymerization of polysiloxanes. (see Kostas, U.S. Pat. No. 5,491,249) This is often employed for the production of some cyclotrisiloxanes and cyclotetrasiloxanes from homopolymers of dialkylsiloxanes, although formation of significant amounts of cyclotrisiloxanes generally requires high temperatures. Mixed cyclosiloxanes, those containing two or more different siloxane repeating units, can be produced in this manner, although isolation of the individual components from the complex mixture can be difficult depending upon the substituents on the repeating units of the cyclosiloxanes and the proportions of these repeating units in the depolymerizing copolymer. (see Buese et al., U.S. Pat. No. 5,247,116)

Processes to prepare specific cyclosiloxanes, particularly cyclotrisiloxanes, include coupling of dichlorosilanes, $R^1R^2SiCl_2$, or dichlorosiloxanes, $Cl(R^1R^2SiO)_x(SiR^3R^4O)_y$ $SiR^5R^6Cl$, with silane diols, $R^7R^8Si(OH)_2$ or siloxane diols, $HO(R^7R^8SiO)_x(SiR^9R^{10}O)_yH$ (where $R^1$, $R^2$, $R^3$, $R^4$, $R^5$, $R^6$, $R^7$, $R^8$, $R^9$, and $R^{10}$ are the same or different and x≥0, y≥0, and x+y≥1). (see Yuzhelevskii et al., *Zhurnal Obshchei Khimii* (1972), 42, (9), 2006-10). The disadvantages of this process include: susceptibility to side products due to reaction with water impurities common in the diols; competing condensation of the diols to larger siloxane diols; corrosiveness to reaction vessels; and potential siloxane redistribution catalyzed by the liberated HCl.

Lewis acid catalyzed processes have been examined that can form large quantities of cyclosiloxanes, particularly cyclotrisiloxanes have been examined. Elimination reactions involving a hydridosiloxane, for example 1,1,3,3,5,5,7,7-octamethyltetrasiloxane, using an aromatic substituted metal halide, permit the formation of a cyclotrisiloxane, for example hexamethylcyclotrisiloxane, with the loss of a dialkylsilane, for example dimethylsilane, $(CH_3)_2SiH_2$, as the main product, although significant amounts of linear dimethylsiloxane polymers, cyclotetrasiloxanes and other cyclosiloxanes can form depending upon the reaction conditions and time between introduction and quenching of the catalyst. (see Rubinsztajn et al., U.S. Pat. No. 7,148,370). Condensation reactions involving a dialkoxysilane, $(H_5C_6)_2Si(OCH_3)_2$ and a dihydrosiloxane 1,1,3,3-tetramethyldisiloxane, using an aromatic substituted metal halide, permit the formation of 1,1-diphenyl-3,3,5,5-tetraamethylcyclotrisiloxane with significant amounts of unidentified linear siloxane oligomers. (see Rubinsztajn et al., US Patent Application Publication No. 2004/0127668) Dehydrocondensation of 0.1 M diphenylsilanediol with an equimolar amount of 1,1,3,3-tetramethyldisiloxane or 1,1,3,3,5,5-hexamethyltrisiloxane using 0.25 M ZnCl$_2$ in DMF gave cyclosiloxane (~30%) and cyclotetrasiloxanes (~50%), respectively, accompanied by a viscous oil. (see Chrusciel et al., *Polish Journal of Chemistry* (1983), 57, 121-7). Hence there remains a need for a process to form mixed cyclosiloxanes, including cyclotrisiloxanes, in high yield and in an easily isolated manner.

BRIEF SUMMARY

Embodiments of the invention are directed to a method for the preparation of cyclosiloxanes by the cyclocondensation between a dihydrosilane or dihydrosiloxane reagent and a dihydroxysilane or dihydroxysiloxane reagent. The method involves introduction of the reagents to a reaction phase comprising a Lewis acid catalyst in solution where the SiH and SiOH functionalities are maintained at a low concentration to inhibit or depress reactions other than the monocyclocondensation. In this manner the high yields of the monocyclization adduct results with little or no formation of linear siloxane impurities or higher molecular weight cyclosiloxanes impurities, allowing relatively easy isolation of a pure cyclosiloxane. In an exemplary embodiment of the invention, 1,1-diphenyl-3,3,5,5-tetramethylcyclotrisiloxane is formed in high yield.

DETAILED DISCLOSURE

Embodiments of the invention are directed to the preparation of cyclosiloxanes by the cyclocondensation of at least one dihydrosilane or dihydrooligosiloxane molecule with at least one dihydroxysilane (silane diol) or dihydroxyoligosiloxane molecule to form a single cyclosiloxane or mixture of cyclosiloxanes of the formula:

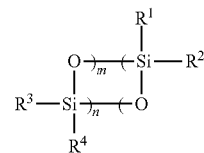

where n is 1 to 6, m is 1 to 6, m+n is 3 to 12, and all $R^1$, $R^2$, $R^3$, and $R^4$ groups are independently: $C_1$ to $C_8$ alkyl; $C_2$ to $C_8$ alkenyl; $C_1$ to $C_8$ halo substituted alkyl having 1 to 13 F, Cl, Br, and/or I; $C_6$ to $C_{10}$ aryl; $C_7$ to $C_{31}$ alkyl mono- or multi-substituted aryl; $C_3$ to $C_9$ trialkylsiloxy; $C_8$ to $C_{26}$ aryldialkylsiloxy, $C_{13}$ to $C_{28}$ alkyldiarylsiloxy, or $C_{18}$ to $C_{30}$ triarylsiloxy. In embodiments of the invention, a plurality of different $R^1$ groups is present in the product cyclosiloxane. In other embodiments of the invention, a plurality of different $R^1$ groups, a plurality of different $R^2$ groups, a plurality of different $R^3$ groups, and/or a plurality of different $R^4$ groups are present in the product cyclosiloxane. The method of preparation involves the cyclocondensation of a dihydrosilane or dihydrosiloxane with a dihydroxysiloxane or the cyclocondensation of a dihydroxysilane or dihydrosiloxane with a dihydrosiloxane in the presence of a Lewis acid by the controlled addition of the reagents such that a "monocyclization" product is primarily the cyclosiloxane resulting from a single pair of the complementary reagents with little or no products from the condensation to linear oligomers from a plurality of reagents or cyclocondensation of a plurality of pairs of complementary reagents.

This monocyclization reaction is one where two complementary reagents condense in a reaction phase comprising the Lewis acid catalyst in solution. Any inert solvent that does not promote reaction other than condensation of the SiH functionality with the SiOH functionality, including undesired side reactions of these functionalities or of the siloxane bonds, can be included in the reaction phase. Solvents comprising OH bonds are generally inappropriate as the solvent included in the reaction phase. Depending on the identity of the $R^1$, $R^2$, $R^3$, and $R^4$, the desired solvent can vary. Solvents that can be employed independently or as a mixture include, but are not limited to: aliphatic hydrocarbons, for example cyclohexane, heptane, or isooctane: aromatic hydrocarbons, for example toluene or xylenes; and siloxanes, for example hexamethyldisiloxane, octamethylcyclotetrasiloxane, or the desired product cyclosiloxane. The monocyclization product can be a single cyclotrisiloxane, cyclotetrasiloxane, cyclopentasiloxane, cyclohexasiloxane, cycloheptasiloxane, cyclooctasiloxane, cyclononasiloxane, cyclodecasiloxane, cycloundecasiloxane, or cyclododecasiloxane. The monocyclization product can be a mixture of siloxanes where the average number of siloxane repeating units is greater than 3 to about 12 wherein each component of the mixture is the monocyclization product from the reaction of two complementary reagents. The reaction temperature can vary over a large range, from 0° C. or lower to temperatures in excess of 100° C. or even 200° C., depending upon the reagents, catalysts and solvents used, as can be appreciated and readily determined by one skilled in the art.

The Lewis acid employed, according to embodiments of the invention, is one that catalyzes a first condensation to an α-hydro-ω-hydroxyoligosiloxane and subsequently catalyzes the intramolecular condensation of the α-hydro-ω-hydroxyoligosiloxane to the desired cyclosiloxane, a monocyclization product, at a sufficiently rapid rate to maintain reactant concentrations at or below a maximum level in the reactive phase where the maximum level depends on the specific size and structure of the reagents. The Lewis acid catalyst promotes a sufficiently rapid reaction such that in combination with a physical or mechanical means allows the control of the reagents' concentrations in a reactive phase, such that the competing intermolecular condensation of the α-hydro-ω-hydroxyoligosiloxane with a dihydrosilane, α,ω-dihydrooligosiloxane, dihydroxysilane, or α,ω-dihydroxyoligosiloxane, or second α-hydro-ω-hydroxyoligosiloxane is discouraged to an appreciable extent or is completely inhibited. The Lewis acid catalyst does not promote siloxane redistribution under the reaction conditions. It should be understood that the position indicators a and w, as used herein, may or may not be the ultimate ends of an oligosiloxanes, but are necessarily the "reactive" ends of the oligosiloxanes, which are silicon atoms having the reactive functionality and are separated by at least one oxygen atom such that the cyclosiloxane resulting from the monocyclization reaction is a cyclotrisiloxane or larger.

According to an embodiment of the invention, the Lewis acid comprises a triphenylborane, $B(C_6H_xX_{5-x})_3$ where x is 0 to 5 and X is independently F, $OCF_3$, $SCF_3$, R, or OR where R is H, $C_1$-$C_{22}$ alkyl or $C_6$-$C_{22}$ aryl. Other catalysts that can be employed, according to embodiments of the invention, are those disclosed in Priou et al. U.S. Pat. No. 6,593,500 and Deforth et al. U.S. Patent Application Publication No. 2003/0139287, which are incorporated herein by reference. The Lewis acid catalysts can be further modified to inhibit its miscibility in a non-reactive phase of the reaction mixture. For example, the Lewis acid catalysts can be attached to a resin where there is little or no affinity of the unreactive phase for the surface of the resin.

In an embodiment of the invention, a dihydroxysilane (silane diol) of the formula: $R^3R^4Si(OH)_2$ is condensed with a dihydrosiloxane of the formula: $H—[R^1R^2SiO]_{n-1}R^1R^2SiH$, where a liquid comprising the oligomeric dihydrosiloxane is added to a suspension comprising the Lewis acid catalyst and the dihydroxysilane in an inert solvent. Although embodiments are not bound by a mechanism, the process is consistent with a quasi-high dilution system where the reaction phase is a solution phase where the solubility of the dihydroxysilane is limited in the reactive phase and the dihydrosiloxane is at a very low concentration because it is added at a rate that is sufficiently slow relative to the rate of its consumption in the catalyzed reaction. The reaction phase has a high concentration of the Lewis acid catalyst, where the Lewis acid is a significant molar fraction or even in excess of the reactive functionalities in the reaction phase. A sufficiently low concentration of the two complementary reagents in the reactive phase solution is maintained in the presence of the catalyst such that after the first condensation of an SiOH with a SiH of the difunctional molecules, intramolecular condensation to the cyclic product occurs, with little or no competing intermolecular condensation to a product consisting of two dihydroxysilane residues and a dihydrosiloxane residue or a product consisting of two dihydrosiloxane residues and a dihydroxysilane residue that ultimately leads to formation of linear oligomers (or polymers) and/or larger cyclosiloxanes, which consist of a plurality of residues of at least one of complementary starting silanes or siloxanes.

Without an effective catalyst, the rate of consumption of the SiOH and SiH functionalities can be inadequate to maintain the sufficiently small concentrations of the functionalities in solution that promote the desired monocyclization reaction. A quasi-dilute system, as employed herein, is one where the products and one or more reagents can be in a high concentration in the reaction vessel, but in the reaction phase, the reactive functionalities are in sufficiently low concentrations, often very low concentrations depending on the desired size of the cyclosiloxane and nature of its substituents, that intramolecular reaction after formation of the α-hydro-ω-hydroxyoligosiloxane is very rapid relative to any intermolecular reaction. The ability to maintain the sufficiently small concentrations of the functionality is dependent upon the relative rates at which the functionalities enter the reaction phase and the rate of reaction. Therefore, a highly active catalyst allows a product profile that effectively depends on the rate at which the reactive functionalities enter the reactive phase. When a reagent is present in a suspension, the suspended phase is not the reactive phase and the suspended reagent enters the reactive phase based on its solubility in the reactive phase. The nonreactive suspended phase can be a liquid or a solid. For example, a crystalline reagent for the cyclization reaction can have a low solubility in the suspending fluid and slowly enter the suspending, reactive phase, as it dissolves. As the reaction progresses the properties of the suspending reactive phase can change, although any change in the solvent effects that may inherently decrease the rate of reaction may be offset by an inherent decrease of the reactant concentrations where the cyclosiloxane product is effectively a diluent of the reactive phase.

In an embodiment of the invention, a dihydrosilane of the formula $R^1R^2SiH_2$ is condensed with a dihydroxysiloxane of the formula HO—$[R^3R^4SiO]_mH$, where a liquid comprising the oligomeric dihydroxysiloxane is added to a suspension comprising the Lewis acid catalyst and the dihydrosilane in an inert solvent. A very low concentration of the two complementary reagents in the reactive phase is maintained such that after the first condensation of an SiOH with a SiH of the difunctional molecules, intramolecular condensation to the cyclic product occurs with little or no intermolecular condensation to a product consisting of two dihydroxysilane residues and a dihydrosiloxane residue, or a product consisting of two dihydrosiloxane residues and a dihydroxysilane residue.

In an embodiment of the invention, a dihydroxysiloxane (siloxane diol) of the formula HO($R^3R^4$SiO)$_m$H is condensed with a dihydrosiloxane of the formula H—[$R^1R^2$SiO]$_{n-1}R^1R^2$SiH, where a liquid comprising the oligomeric dihydrosiloxane is added to a suspension comprising the Lewis acid catalyst and the dihydroxysiloxane in an inert solvent. A very low concentration of the two complementary reagents in solution is maintained such that the after the first condensation of an SiOH with a SiH of the difunctional molecules, intramolecular condensation to the cyclic product occurs with little or no intermolecular condensation to a product consisting of two dihydroxysiloxane residues and a dihydrosiloxane residue, or a product consisting of two dihydrosiloxane residues and a dihydroxysiloxane residue.

In one embodiment, a dihydrosiloxane of the formula H—[$R^1R^2$SiO]$_{n-1}R^1R^2$SiH, is condensed with a dihydroxysiloxane (siloxane diol) of the formula HO($R^3R^4$SiO)$_m$H, where a liquid comprising the oligomeric dihydroxysiloxane is added to a suspension comprising the Lewis acid catalyst and the dihydrosilane in an inert solvent. A very low concentration of the two complementary reagents in solution is maintained such that after the first condensation of an SiOH with a SiH of the difunctional molecules, intramolecular condensation to the cyclic product occurs with little or no intermolecular condensation to a product consisting of two dihydroxysiloxane residues and a dihydrosiloxane residue, or a product consisting of two dihydrosiloxane residues and a dihydroxysiloxane residue.

In an embodiment of the invention, a dihydrosilane or a dihydrosiloxane is condensed with a dihydroxysiloxane or a dihydroxysilane, where at least three silicon atoms are present in an intermediate formed after the first condensation, when one or more liquids comprising the dihydrosilane or dihydrosiloxane and/or dihydoxysiloxane or dihydroxysilane, and optionally a solvent, are added to solution comprising the Lewis acid catalyst and an inert solvent. A very low concentration of the two complementary reagents in the reaction phase is maintained by controlling the rate of addition, such that the after the first condensation of an SiOH with a SiH of the difunctional molecules, intramolecular condensation to the cyclic product occurs with little or no intermolecular condensation to a product consisting of two dihydroxysiloxane residues and a dihydrosiloxane residue, or a product consisting of two dihydrosiloxane residues and a dihydroxysiloxane residue. Complementary reagents can be within a single liquid or in separate liquids, which can be added in a manner where the reagents are diluted rapidly such that contact with the Lewis acid catalyst and subsequent reaction does not occur prior to dilution. When two or more sites of addition are included in the reactor, complementary reagents can be introduced from different sites to facilitate dilution before reaction.

In an embodiment of the invention, a dihydrosilane or dihydrosiloxane is condensed with a dihydroxysiloxane or dihydroxysilane, where at least three silicon atoms are present in an intermediate formed after the first condensation, when one or more types of liquid and/or solid phase comprising the dihydrosilane or dihydrosiloxane and/or dihydroxysiloxane or dihydroxysilane, and optionally a solvent or solid binder, are suspended in an at least partially immiscible solution comprising the Lewis acid catalyst and an inert solvent. A very low concentration of the two complementary reagents is maintained within the reaction phase due to the rate and extent of partitioning between the suspended phase or phases and the reaction phase such that after the first condensation of an SiOH with a SiH of the difunctional molecules, intramolecular condensation to the cyclic product occurs with little or no intermolecular condensation to a product consisting of two dihydroxysiloxane residues and a dihydrosiloxane residue, or a product consisting of two dihydrosiloxane residues and a dihydroxysiloxane residue.

According to embodiments of the invention, the suspended reagent or reagents can be in a liquid or solid phase where the liquid phase can be a pure liquid reagent, a liquid consisting of both reagents or a solution comprising one or both reagents as long as that liquid is immiscible with the reactive phase. A suspended solid phase can be the reagent in a crystalline or amorphous solid phase or can be the reagent within a solid binder that absorbs the reagent and allows its slow extraction into the reactive phase. According to embodiments of the invention, both reagents can be added to a reactive phase from one or more external reservoirs through one or more ports such that their rate of addition is slow relative to the consumption of the reagents in the presence of the reactive phase comprising the Lewis acid catalyst. The method according to embodiments of the invention can be carried out in a batch reactor or a continuous reactor.

METHODS AND MATERIALS

Example 1

Synthesis of 1,1-Diphenyl-3,3,5,5-tetramethylcyclotrisiloxane ("Diphenyl-D3")

In a dry 2 L round bottom flask fitted with a mechanical stirrer, condenser, thermocouple probe with temperature control, heating mantle and nitrogen over-gas was placed 216 g (1.0 mole) diphenylsilanediol (DPSD) and 400 g xylenes. The mixture was heated to 40° C. and stirred to partially dissolve the DPSD. Using a syringe, 1.0 ml of a 5% tris(pentatluorophenyl)boron in xylenes solution was added to the flask resulting in a boron complex concentration of 50 ppm. From an addition funnel was added 134 g (1.0 mole) tetramethyldisiloxane (TMDSO) at a rate that maintained a steady slow evolution of hydrogen gas. The addition continued for about 1 hour at 40 to 60° C. After complete addition of TMDSO, the reaction mixture was stirred at 60° C. for an hour. Analysis of the reaction mixture by FTIR spectroscopy showed no SiH signal at ~2150 cm$^{-1}$. Complete conversion of the tetramethyldisiloxane and the production of 96% Diphenyl-D3 with small amounts of 1,1-diphenylhexamethylcyclotetrasiloxane (Diphenyl-D4; 0.8%), tetraphenyltetramethylcyclo-tetrasiloxane (Tetraphenyl-D4, 1.0%) and 1,1,7,7-tetraphenyloctamethylcyclohexasiloxane (Tetraphenyl-D6, 1.4%) was indicated by GC analysis. The acid catalyst was neutralized by the addition of 1.0 g of magnesium oxide to the reaction mixture with stirring for 30 minutes. The MgO was filtered from the cyclosiloxane solution and the solvent was removed from the cyclosiloxane mixture in a 2 L round bottom flask using a rotary evaporator at 60° C. and <5 mmHg. The residue was dissolved in 300 g of warm hexamethyldisiloxane and filtered. Diphenyl-D3 crystallized from solution upon cooling to room temperature. An initial crop of crystals of approximately 170 g was isolated from the mother liquor. Concentration of the mother liquor and cooling to form additional Diphenyl-D3 crystals gave a total yield of 270 g (80%) of Diphenyl-D3. Recrystallization from hexamethyldisiloxane gave Diphenyl-D3 with a melting point of 65-67° C. The structure was confirmed by $^1$H NMR analysis and GC analysis of a THF solution of the product indicated a purity of 99.2%.

Comparative Example 1

Attempted Synthesis of Diphenyl-D3 Using Palladium on Carbon as Catalyst

In a dry 250 ml round bottom flask fitted with a magnetic stirrer, condenser, thermocouple probe with temperature control, heating mantle and nitrogen over-gas was placed 21.6 g (0.10 mole) DPSD and 40 g xylenes. The mixture was heated to 40° C. and stirred to partially dissolve the DPSD and 0.20 g of 5% palladium on carbon was added resulting in a suspension with a Pd content of 130 ppm. An addition funnel was loaded with 13.4 g (0.10 mole) tetramethyldisiloxane and approximately 3 g of the tetramethyldisiloxane was added to the catalyzed mixture. No hydrogen off-gassing was observed. The reaction was heated to 90° C. for 16 hours and FTIR analysis of the reaction mixture showed the presence of SiH at 2150 cm$^{-1}$. A GC analysis of the reaction mixture showed that most of the tetramethyldisiloxane remained, with only 1.1% Diphenyl-D3 formed along with 1.2% Diphenyl-D4.

Comparative Example 2

Attempted Synthesis of Diphenyl-D3 Using Tris(triphenylphosphine) Rhodium Chloride as Catalyst In a dry 250 ml round bottom flask fitted with a magnetic stirrer, condenser, thermocouple probe with temperature control, heating mantle and nitrogen over-gas was placed 21.6 g (0.10 mole) DPSD and 40 g xylenes. The mixture was heated to 40° C. and stirred to partially dissolve the DPSD. Using a syringe, 0.2 ml of a 5% tris(triphenylphosphine) rhodium chloride solution in xylenes was added to the reaction flask to yield a Rh content of ~30 ppm. An addition funnel was loaded with 13.4 g (0.10 mole) tetramethyldisiloxane and approximately 3 g of the tetramethyldisiloxane was added with no apparent hydrogen off-gassing. The reaction mixture was heated to 80° C. for 1 hour and a slight off-gassing was observed. An additional 1.0 ml of 5% tris(triphenylphosphine) rhodium chloride solution in xylenes was added to give a total Rh content of ~180 ppm and the reaction mixture was heated at 80° C. for 16 hour. A large amount of tetramethyldisiloxane and no formation of Diphenyl-D3 were indicated by GC analysis.

Comparative Example 3

Attempted Synthesis of Diphenyl-D3 Using Anhydrous Zinc Chloride as Catalyst In a dry 250 ml round bottom flask fitted with a magnetic stirrer, condenser, thermocouple probe with temperature control, heating mantle and nitrogen over-gas was placed 21.6 g (0.10 mole) DPSD and 40 g xylenes. The mixture was heated to 40° C. and stirred to partially dissolve the DPSD. Under nitrogen, 0.14 g (1.0 mmol) anhydrous zinc chloride was added to the flask and an addition funnel was loaded with 13.4 g (0.10 mole) tetramethyldisiloxane. Upon addition of approximately 3 g of the tetramethyldisiloxane, no off-gassing was observed. The reaction was heated to 60° C. for 1 hour and a slight off-gassing was observed. An additional 2.0 g anhydrous zinc chloride was placed in the flask to increase the ZnCl to 15.3 mmol and the reaction mixture was heated to 60° C. and maintained for 16 hours. The presence of considerable residual tetramethyldisiloxane was indicated by FTIR analysis, which showed a large peak for SiH ~2150 cm$^{-1}$.

Example 4

Synthesis of 1,1-Diphenyl-3,3,5,5,7,7-hexamethylcyclotetrasiloxane ("Diphenyl-D4")

In a dry 250 L round bottom flask fitted with a magnetic stirrer, condenser, thermocouple probe with temperature control, heating mantle and nitrogen over-gas was placed 21.6 g (0.10 mole) DPSD and 40 g xylenes. The mixture was heated to 40° C. and stirred to partially dissolve the DPSD. Using a syringe, 0.2 ml of a 5% tris(pentafluorophenyl)boron in xylenes was added to yield a boron complex concentration of 100 ppm in the mixture. From an addition funnel was added 20.8 g (0.10 mole) 1,1,3,3,5,5-hexamethyltrisiloxane (M'DM') at a rate that maintained a steady slow evolution of hydrogen gas. The addition continued for about 1 hour at 40-60° C. Upon complete addition of the M'DM', the reaction mixture was stirred at 60° C. for 1 hour. When an FTIR analysis of the reaction mixture displayed no signal for SiH at ~2150 cm$^{-1}$, 0.2 g of magnesium oxide was added to neutralize the catalyst, and the reaction mixture was stirred for 30 minutes. The mixture was filtered into a 250 ml round bottom flask, and the solvent was removed using a rotary evaporator at 80° C. and <5 mmHg. A residue of 28.4 g was recovered that was 82% Diphenyl-D4 by GC analysis. A GPC analysis did not show the presence of polymer in the residue. The residue was flash distilled with a kugelrohr at 175° C. and 0.1 mmHg to give 23 g (55% yield) of 96.6% Diphenyl-D4 according to GC analysis.

Example 5

Synthesis of 1,1-Diphenyl-3,3,5,5,7,7,9,9-octamethylcyclopentasiloxane ("Diphenyl-D5")

In a dry 100 L round bottom flask fitted with a magnetic stirrer, condenser, thermocouple probe with temperature control, heating mantle and nitrogen over-gas was placed 10.8 g (0.05 mole) DPSD and 20 g xylenes. The mixture was heated to 40° C. and stirred to partially dissolve the DPSD. Using a syringe, 0.1 ml of a 5% tris(pentafluorophenyl)boron in xylenes was added to yield a boron complex concentration of 100 ppm in the mixture. From an addition funnel was added 14.1 g (0.05 mole) 1,1,3,3,5,5,7,7-octamethyltetrasiloxane (M'DDM') at a rate that maintained a slow steady evolution of hydrogen gas. The addition continued for about 1 hour at 40-60° C. Upon complete addition of the M'DDM', the reaction mixture was stirred at 60° C. for 1 hour. When an FTIR analysis of the reaction mixture displayed no signal for SiH at ~2150 cm$^{-1}$, 0.1 g of magnesium oxide was added to neutralize the catalyst, and the reaction mixture was stirred for 30 minutes. The mixture was filtered into a 100 ml round bottom flask, and the solvent was removed using a rotary evaporator at 90° C. and <5 mmHg. A residue of 18.2 g was shown to be 84% Diphenyl-D5 by GC analysis. A GPC analysis showed the presence of some polymer in the residue.

Example 6

Synthesis of 1,1-Diphenyl-bis-3,5-trimethylsiloxy-3,5-dimethylcyclotrisiloxane ("Diphenyl-DT2M2")

In a dry 100 L round bottom flask fitted with a magnetic stirrer, condenser, thermocouple probe with temperature control, heating mantle and nitrogen over-gas was placed 10.8 g (0.05 mole) DPSD and 20 g xylenes. The mixture was heated to 40° C. and stirred to dissolve the DPSD. Using a syringe, 0.1 ml of a 5% tris(pentafluorophenyl)boron in xylenes was added to yield a boron complex concentration of 100 ppm in the suspension. From an addition funnel was added 14.1 g (0.05 mole) 1,1,1,3,5,7,7,7-octamethyltetrasiloxane (MD'D'M) at a rate that maintained a slow steady evolution of hydrogen gas. The addition continued for about 1 hour at 40-60° C. After complete addition of the MD'D'M, the reaction mixture was stirred at 60° C. for 1 hour. An FTIR analysis of the reaction mixture displayed no SiH (2150 cm$^{-1}$). After a GC analysis indicated a large quantity of Diphenyl-DT2M2 and only a trace of octamethylcyclotetrasiloxane (D4), 0.1 g of magnesium oxide was added to neutralize the catalyst and the reaction mixture was stirred for 30 minutes. The mixture was filtered into a 100 ml round bottom flask, and the solvent was removed on a rotary evaporator at 90° C. and <5 mmHg to yield a residue of 21.6 g of residue that was 96% Diphenyl-DT2M2 (2 isomers) by GC analysis. A GPC analysis showed a trace of polymer.

Example 7

Synthesis of 1,1,5,5-Tetraphenyl-3,3,7,7-tetramethyl-cyclotetrasiloxane ("Tetraphenyl-D4")

In a dry 100 L round bottom flask fitted with a magnetic stirrer, condenser, thermocouple probe with temperature control, heating mantle and nitrogen over-gas was placed 13 g (0.06 mole) DPSD and 30 g xylenes. The mixture was heated to 40° C. and stirred to dissolve the DPSD. Using a syringe, 0.2 ml of a 5% tris(pentafluorophenyl)boron in xylenes was added to yield a boron complex concentration of 150 ppm in the solution. From an addition funnel was added 22.2 g (0.06 mole) 3,3-Diphenyl-1,1,5,5-tetramethyltrisiloxane (M', D$^{Ph2}$M') at a rate that maintained a slow steady evolution of hydrogen gas. The addition continued for about 1 hour at 40-60° C. Once addition was completed, the reaction mixture was stirred at 60° C. for an hour. When an FTIR analysis of the reaction mixture displayed no signal for SiH at ~2150 cm$^{-1}$ and a GC analysis showed about a 79% yield of Tetraphenyl-D4, 0.1 g of magnesium oxide was added to neutralize the catalyst and the reaction mixture was stirred for 30 minutes. The mixture was filtered into a 100 ml round bottom flask and the solvent was removed using a rotary evaporator at 90° C. and <5 mmHg leaving 26.4 g of white crystals in an oil that was ~76% Tetraphenyl-D4 by GC analysis. Recrystallization from hexamethyldisiloxane afforded 13.6 g of Tetraphenyl-D4 as white crystals with m.p. 131-133° C. The structure was confirmed by $^1$H NMR analysis.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

I claim:

1. A method for preparing cyclosiloxanes comprising:
   providing a first reagent consisting of a dihydrosilane, dihydrosiloxane, or combination thereof of the structure:

H—[R$^1$R$^2$SiO]$_{n-1}$R$^1$R$^2$SiH, where n is 1 to 6, and R$^1$ and R$^2$ are independently: C$_1$ to C$_8$ alkyl; C$_2$ to C$_8$ alkenyl; C$_1$ to C$_8$ halo substituted alkyl having 1 to 13 F, Cl, Br, and/or I; C$_6$ to C$_{10}$ aryl; C$_7$ to C$_{31}$ alkyl mono- or multi-substituted aryl; C$_3$ to C$_9$ trialkylsiloxy; C$_8$ to C$_{26}$ aryldialkylsiloxy, C$_{13}$ to C$_{28}$ alkyldiarylsiloxy, or C$_{18}$ to C$_{30}$ triarylsiloxy;
   providing a second reagent consisting of a dihydroxysilane, dihydroxysiloxane, or combination thereof of the structure:

HO—[R$^3$R$^4$SiO]$_m$H, where m is 1 to 6 and R$^3$ and R$^4$ are independently: C$_1$ to C$_8$ alkyl; C$_2$ to C$_8$ alkenyl; C$_1$ to C$_8$ halo substituted alkyl having 1 to 13 F, Cl, Br, and/or I; C$_6$ to C$_{10}$ aryl; C$_7$ to C$_{31}$ alkyl mono- or multi-substituted aryl; C$_3$ to C$_9$ trialkylsiloxy; C$_8$ to C$_{26}$ aryldialkylsiloxy, C$_{13}$ to C$_{28}$ alkyldiarylsiloxy, or C$_{18}$ to C$_{30}$ triarylsiloxy;
   providing a reaction phase comprising a Lewis acid catalyst and a solvent; and
   combining the first reagent and the second reagent over a period of time in the reaction phase to produce an initial condensation product, H—[R$^1$R$^2$SiO]$_n$-[R$^3$R$^4$SiO]$_m$H, which initial condensation product undergoes intramolecular condensation to form a cyclosiloxane of the structure:

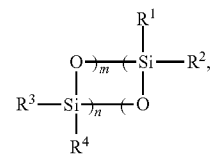

wherein the product produced by the reaction contains about 24% or less of higher molecular weight siloxane oligomers.

2. The method according to claim 1, wherein the Lewis acid comprises B(C$_6$H$_x$X$_{5-x}$)$_3$ where x is 0 to 5 and X is independently F, OCF$_3$, SCF$_3$, R, or OR where R is H, C$_1$-C$_{22}$ alkyl or C$_6$-C$_{22}$ aryl.

3. The method according to claim 1, wherein the first reagent and/or the second reagent is/are provided as a suspension in the reaction phase.

4. The method according to claim 1, wherein the first reagent and/or the second reagent is/are provided by controlled addition to the reaction phase from a reservoir.

5. The method according to claim 1, wherein the second reagent is diphenyldisilanol (DPDS), and wherein the DPDS is provided as a solid suspension in the reaction phase.

6. The method according to claim 5, wherein the solvent comprises xylenes.

7. The method according to claim 5, wherein the Lewis acid comprises tris(pentafluorophenyl)boron.

8. The method according to claim 5, wherein the first reagent comprises 1,1,3,3-tetramethyldisiloxane.

9. The method according to claim 5, wherein the first reagent comprises H—[(H$_3$C)$_2$SiO]$_{n-1}$(H$_3$C)$_2$SiH, where n is 3 or 4.

10. The method according to claim 5, wherein the first reagent comprises (H$_3$C)$_3$SiO—[(H$_3$C)HSiO]$_2$—Si(CH$_3$)$_3$.

11. The method according to claim 5, wherein the first reagent comprises H(H$_3$C)$_2$SiO(H$_5$C$_6$)$_2$SiO(H$_3$C)$_2$SiH.

12. The method according to claim 1, wherein the second reagent comprises HO(H$_3$C)$_2$SiO(H$_5$C$_6$)$_2$SiO(H$_3$C)$_2$SiOH.

* * * * *